United States Patent [19]

Saint-Firmin

[11] 4,241,536

[45] Dec. 30, 1980

[54] EMBRYOGENESIS IN VITRO, INDUCTION OF QUALITATIVE AND QUANTITATIVE CHANGES IN METABOLITES PRODUCED BY PLANTS AND PRODUCTS THEREOF

[76] Inventor: Annette R. Saint-Firmin, 2407 #L. Wesvill Ct., Raleigh, N.C. 27607

[21] Appl. No.: 922,681

[22] Filed: Jul. 7, 1978

Related U.S. Application Data

[63] Continuation-in-part of Ser. No. 849,952, Nov. 9, 1977, abandoned, and a continuation-in-part of Ser. No. 849,953, Nov. 9, 1977, abandoned.

[30] Foreign Application Priority Data

Nov. 10, 1976 [GB] United Kingdom ............... 46866/76
Nov. 19, 1976 [GB] United Kingdom ............... 48403/76

[51] Int. Cl.$^3$ .................... A01G 31/00; C12K 9/00
[52] U.S. Cl. ......................................................... 47/58
[58] Field of Search ..................................... 47/58, 1.2

[56] References Cited

U.S. PATENT DOCUMENTS

| | | | |
|---|---|---|---|
| 2,747,334 | 5/1956 | Routien et al. ............... | 47/58 |
| 3,704,546 | 12/1972 | Hardy et al. ................ | 47/58 |

FOREIGN PATENT DOCUMENTS

| | | | |
|---|---|---|---|
| 2533437 | 2/1976 | Fed. Rep. of Germany ............. | 47/58 |
| 2603588 | 8/1976 | Fed. Rep. of Germany ............. | 47/58 |
| 1387821 | 3/1975 | United Kingdom ................. | 47/58 |

OTHER PUBLICATIONS

Growth and Development—, Steward et al., Science, vol. 143, Jan. 1964, pp. 20–27.
Haploid Plants—, Nitsch et al., Science, vol. 163, Jan. 1969, pp. 85–87.
Factors Influencing Morphogenesis—, Thomas et al., Ann. of Botany 36, 1972, pp. 239–247.
Role of the Generative—, Raghavan, Science, vol. 191, Jan. 1976, pp. 388–389.
Acta Botanica Sinica 20, Series 3, 1978, pp. 204–209.
Morphogenetic Responses—, Krikorian et al., Science, vol. 200, Apr. 1978, pp. 67–68.
Production of Natural Substances—Misana, Tokyo, Res. Lab., Kyowa Hakko Hogyo Co. Ltd., Machidashi, Tokyo, Japan.

*Primary Examiner*—Robert E. Bagwill

[57] ABSTRACT

The process of embryogenesis in vitro whereby single embryonic cells are obtained and from which normal, healthy plants can be produced. The process is capable of making, in vitro, any metabolite producible by the whole plant, for example tropane alkaloids. This process of embryogenesis in vitro comprises the steps of inducing from any plant material, for example, from plant material of the families Solanaceae and Erythroxylaceae, the formation of a partially dedifferentiated tissue comprised of mitotic cells, such as callus and tumor cells, preparing a cell culture therefrom, rejuvenating the cells to return them to the embryonic state through controlled environmental conditions, for example, in the case of Solanaceae and Erythroxylaceae through temperature and light, differentiating the embryonic cells to restore the ageing process thereof whereby the tissue function, as part of their normal growth pattern, will give embryos and consequently metabolites. At this point qualitative and quantitative changes in the pattern of the metabolites can be induced.

The process of producing a non-cyto-toxic-metabolite, from plant material.

The process of obtaining mixed fermentation of cultured cells from higher plants whereby a differentiated cell producing the messenger undergoes embryogenesis.

The process of inducing symbiotic relationship between cultured cells of higher plants and microorganisms for producing physiologically active compounds as for example anti-neoplastic agents.

The process of inducing tumor in plant by stimulating the endogenic hormone of the cells with an exogenic supply.

The novel products obtained by the foregoing processes.

20 Claims, 2 Drawing Figures

FIG. 1

FIG. 2

Energy Distribution at Various Wave Lengths. In Ultra-Violet Range.

EMBRYOGENESIS IN VITRO, INDUCTION OF QUALITATIVE AND QUANTITATIVE CHANGES IN METABOLITES PRODUCED BY PLANTS AND PRODUCTS THEREOF

REFERENCE TO PRIOR APPLICATIONS

This application is a continuation-in-part of my prior U.S. Pat. Applications Ser. Nos. 849,952 and 849,953, both filed Nov. 9, 1977 and now abandoned.

This invention relates to embryogenesis in vitro, induction of qualitative and quantitive changes in metabolites produced by plants and products thereof.

BACKGROUND OF THE INVENTION

Many efforts have been made in the past to produce plants from single cells. For example, British Patent Specification No. 1,387,821 discloses producing chemical plant metabolites by suspension culture and uses the process of organogenesis. The process is carried out by a sequential differentiation, in other words, by organs regeneration which occurs when the nutrient provided to the culture shows a decreasing auxin level.

The process can be schematically summarized: Explant callus cell clusters or single cells plant organ primordia.
"root primordia"
"shoot primordia"
"pellet"

This regeneration taught by this publication is carried out under "subdued light" conditions with the temperature of the nutrient varying between 15° C. and 35° C. The process requires more than one year duration.

Metabolites such as tropane alkaloids are found in nature in various members of the plant family Solanaceae and Erythroxylaceae from which th first extractions occurred from *Atropa belladonna* and thus, the derivation of the alternative designation atropine group. The four main tropane alkaloids are atropine, hyoscine (scopolamine), hyoscyamine, (solanaceae) and cocaine (Erythroxylaceae).

The alkaloid atropine can be isolated from the plant deadly nightshade (*Atropa belladonna* ). The related alkaloid scopolamine (hyoscine) which has "truth drug" properties can be isolated from the plant species Scopolia spp. or Duboisia spp. Hyoscyamine can be isolated from plants of the species Hyoscyamus spp. The fourth main member of the tropane group alkaloids is cocaine and is mostly isolated from plants of the species Erythroxylon.

These alkaloids are also found in the plant *Hyoscyamus niger,*—which grows in Europe,—together with various other chemically related alkaloids of the group in minor amounts. However, the alkaloid content of *Hyoscyamus niger* is too low for commercial extraction. Although the yield of these alkaloids is not so low in plants of the tribe Daturae spp. these plants also are not used as raw material for commercial extraction.

The tropane alkaloids have well known medicinal properties. Indeed it is related that, as long ago as 1500 BC, plants producing alkaloids of the atropine group are used for criminal, magic or medicinal purposes. The tropane alkaloids are in demand not only by virtue of their own medicinal properties but also as starting materials for preparing other active compounds for use in medicine and in biological research.

Various members of the plant families Solanaceae and Erythroxylaceae are known to contain metabolites such as atropine, scopolamine, hyoscyamine, cocaine and related tropane alkaloids, more particularly plants of the species Hyoscyamus spp. Duboisia spp. and Erythroxylon spp. Besides *Hyoscyamus niger* mentioned above, there can also be mentioned *Hyoscyamus muticus* L. and *Hyoscyamus aureus* L. Hyoscyamus pusillus, Hyoscyamus albus, Withania, Solandra, and Anthocercis and *Datura innoxia, Datura stra monium, Datura tatula, Datura meteloiides, Datura sanguinea.*

Since the plants which are known to be rich in tropane alkaloids mostly originate from tropical or subtropical regions, current commercial methods of extracting atropine group alkaloids from natural sources rely on dried plant material as the raw material. Such dried material can be produced by oven-drying, for example at approximately 40° C., or by freeze-drying. However this is a relatively inefficient and expensive method of obtaining the desired alkaloids since one must wait for the plant to reach maturity before harvesting and drying of the plant can take place. The yield of alkaloids is affected by the climatic and edaphic factors under which the crop is grown. In particular the crops prone to storm damage, storms being generally more frequent in the tropics than in the more temperate regions such as Europe, and such storm damage may tend to reduce the alkaloid content of the plants. Furthermore, the percentage of alkaloids in different crops of the same plant may vary considerably from year to year and from location to location due to differences, for example, in rainfall and in soil conditions under which the crop is grown. Moreover, the percentage of total alkaloids in the dried plant material may vary considerably at the time of extraction due to differences between chronological and physiological age, as well as to variations in storage conditions and in the conditions under which the harvested plants are transported.

In addition to the major tropane alkaloids discussed above, and minor alkaloids as example: littorine, hygrine, cuscohygrine, tigloidine, apohyoscine, noratropine, norhyoscine, apoatropine, and the tigloryl esters, other metabolites produced by plants have known value, exhibit worthwhile properties, or may prove valuable if an opportunity were available to collect significant quantities of same and to test. Therefore, a technique that would enhance the yield of any given metabolite or enable its creation in relatively short time frames would be welcome indeed. Also no one to date has been able to achieve embryogenesis in vitro related to production of physiologically active compound despite the extensive effort expended to date by the scientific community.

BRIEF SUMMARY OF THE INVENTION

I have now discovered a process of embryogenesis in vitro whereby single embryonic cells are obtained and from which normal, healthy plants can be produced. The process is capable of making, in vitro, any metabolite producible by the whole plant, for example tropane alkaloids. This process of embryogenesis in vitro comprises the steps of inducing from any plant material, for example, from plant material of the families Solanaceae and Erythroxylaceae, the formation of a partially dedifferentiated tissue comprised of mitotic cells, such as callus and tumor cells, preparing a cell culture therefrom, rejuvenating the cells to return them to the embryonic state through controlled environmental conditions, for example, in the case of Solanaceae and Erythroxylaceae through temperature and light, differentiating the embryonic cells to restore the ageing process thereof whereby the tissue function, as part of their normal growth pattern, will give embryos and consequently metabolites. At this point qualitative and quantitative changes in the pattern of the metabolites can be induced.

The novel process of embryogenesis in vitro is obtained by the complete differentiation of a single somatic or generative cell from the embryonic stage of the cell to the plant embryo or the seedling. This had been achieved by the adequate manipulation of the climatic and edaphic factors, which means the environment of the culture room and of the culture itself. Specifically, the climatic factors include:

the energy level produced by the light source provided to the culture;
the spectrum of the provided light;
the photoperiod; and
the ambient temperature.

The environment of the culture itself or the edaphic factors inlude:

the composition of the nutrients;
the pH of the nutrients; and
the $O_2/CO_2$ ratio of the culture.

My novel process comprises the following steps:
Step I: providing mitotic cells:
(a) by culture of explants including the meristem of the shoot or the meristem of the root from the chosen plant which induces a callus.
(b) from seeds by inducing the formation of a tumor.
Step II: providing embryonic cells:
The mitotic cells are rejuvenated by the control of the above designated environmental factors.
Step III: Differentiation of the embryonic cells
The embryonic cells under the chosen environment undergo differentiation and plant embryos, then seedlings are obtained with the understanding that the chosen stage or termination is according to the pursued goal: biochemical work or plant multiplicaton or plant improvement or other types of research or utilization such as chemicals, or food (protein) production.

I have also discovered a process of producing a non-cyto-toxic-metabolite, from plant material, for example, plant material of the families Solanaceae and Erythroxylaceae (the genera Hyoscyaminae and Duboisiae being the richest). The metabolite is a growth regulator, has antibacterial properties, controls mitosis, is effective for inducing cell differentiation in plant cells, and possibly is an anti-neoplastic agent. The metabolite apears to be a type of "messenger" related to 5-Hydroxyferulic acid (5HFA). This compound is obtained by stimulating the phytochrome and inducing de novo synthesis of PAL (phenylalanine-ammonia-lyase) to obtain what is believed to be a cinnamic derivative.

I have also discovered a process of obtaining mixed fermentation of cultured cells from higher plants whereby a differentiated cell producing the messenger (metabolite) undergoes embryogenesis (as for example, the differentiated cell of plant from the Solanaceae or Erythroxylaceae families) and induces thereby embryogenesis in the partner cell (as for example, an originally undifferentiated cell of plant from Catharanthus, Papaver, Wheat, or Acer). This is generally accomplished in one of two ways.

In one way, a partially purified extract of the subject metabolite is mixed with the nutrient provided to the cells to be differentiated; a second way is by an inoculation of the two types of cells in the same flask.

I have also discovered a process of inducing symbiotic relationship between cultured cells of higher plants and microorganisms for producing physiologically active compounds, as for example, anti-neoplastic agents. Thus, cells from the plants *Tripterygium wilfordii, Putterlichia verrucosa,* or *Maytenus buchananii* are cultivated with microorganisms such as fungi imperfecti whereupon metabolites are generated which are physiologically active. Also, by using any explant in culture preferably in a liquid medium and innoculating the culture with the microorganisms.

I have also discovered a process of inducing tumor in plant at an early stage of its development by stimulating the endogenic hormone of the plantlet with an exogenic supply.

I have discovered novel products which are obtained by my novel processes.

The invention can be used to obtain any metabolite such as ansa-macrolides, steroids, protein and tropane alkaloids via a cell culture as described which can be grown reproducibly under controlled environmental conditions to give even higher alkaloid yields than can be obtained in good dried plant material.

DETAILED DESCRIPTION OF THE PREFERRED EMBODIMENT

According to the present invention there is provided a process for embryogenesis in vitro as applied to any plant and also for the purpose of manufacturing any metabolite producible by plant. Although the process may be applied to any plant for any purpose, for illustration of the invention, it will be described specifically with reference to certain plants and for producing a specific metabolite, in this instance, tropane alkaloids, Thus, in the preferred case, the process comprises the steps of providing plant material of a tropane alkaloid-producing plant of the families Solanaceae and Erythroxylaceae, inducing mitotic cell formation from the said plant material, preparing a cell culture therefrom and rejuvenating the cells to restore them to the embryonic state by a controlled environment, and then differentiating the embryonic cells to start the normal ageing process, and thereafter at an appropriate time, harvesting the normally differentiated cells to recover tropane alkaloids therefrom. The process, however, has general application.

Preferably the plant material (for tropane alkloids) is from a plant of the family Solanaceae including one of the following genera of plants: Solanae, Daturae, Salpiglossidae, Nicandrae, and Cestrae (Classification of Wettstein (1887), Emberger (1960), Melchior (1964) or of one of the species Hyoscyamus spp. and Duboisia spp. Especially preferred are plants of the species Hyoscyamus spp. or Duboisia spp. Worthy of particular mention are *Hyoscyamus muticus* L. and *Hyoscyamus aureus* L. Examples of suitable members of the species Duboisia spp. are *Duboisia leichardtii, Duboisia hopwoodii,* and *Duboisia myoporoides.* As noted, the plant may be one of the family Erythroxylaceae including the genera Erythroxylon spp., Celastraceae including *Tripterygium wilfordii, Putterlichia verrucosa,* and *Maytenus buchananii* or Apocynaceae including Catharanthus sp, Papaveraceae including Papaver spp. and Scopolia spp., Solanum spp., Nicotiana spp. also from the Solanaceae family.

In addition, the invention has general applicability to plants including as examples carrots, tomatoes, mints, strawberries, tulips, rudbeckia, snapdragons, larkspurs, roses, tobacco, Phaseolus, Acer, soy beans, Ricinus and wheat.

The plant material may take a variety of explant forms, for example leaf, stem, root, anther, pollen grain, petal, hair material, vegetative meristem from shoot or floral meristem from shoot, and meristem of the root. Thus, suitable plant material includes as explant internodal stem material, preferably from floral stems. Alternatively, and preferably, the plant material comprises seeds or seedlings.

Mitotic cell formation can be induced by various known methods, or by my inventive method. One method is to induce callus formation and comprise cutting material from a whole plant, and contacting the resulting explant with a suitable culture medium, preferably under controlled aseptic environmental conditions. This method is suitable for use, for example, with stem segment explants. Preferably internodal segment explants are taken and contacted with the culture medium. Inter-nodal floral stem segments are particularly suitable for this purpose. Under favourable conditions callus form at the cut ends of the explants. Using floral stem explants it is not necessary to add any auxin, cytokinin or gibberillin to the culture medium. If the explant originates from another part of the plant, it will usually be desirable to incorporate in the culture medium during callus formation a mixture of an auxin and a cytokinin in low concentration.

For best results the mother plant from which the explant is taken should be in good physiological condition. I prefer to grow the mother plant by hydroponic culture using a conventional mineral solution of controlled pH, i.e. of pH about 5.1 to about 5.4. I also prefer to control the temperature and the light conditions. Humidity conditions of about 70% relative humidity are suitable.

An alternative, and preferred method, for inducing mitotic formation involves my novel process comprising hormonal treatment of seedlings of the chosen plant. According to this novel method, seeds of the plant are allowed to germinate and produce seedlings whose growth is modified by a first auxin. After a period of growth under the influence of the chosen first auxin, the seedlings are then subjected to the influence of a second auxin. If the two auxins are appropriately chosen, tumor is induced within a further period of growth after the change to the second auxin without any need to cut the seedling.

Thus, according to my invention a preferred process comprises treating seedlings with a first auxin, allowing roots to develop under the influence of the first auxin, treating the thus-treated seedlings with a second auxin different from the first auxin, forcing mitotic tissue (tumor) to develop. Using this inventive and preferred dual auxin treatment I have found that the period required for obtaining a useful result, such as a desired metabolite, for example a tropane alkaloid, starting from seeds is shorter than if I use the route which involves inducing callus from an explant (using, for example, an inter-nodal floral stem segment explant). Although both are mitotic cells, tumor is different from callus particularly with respect to the level of differentiation and I have found tumor easier to rejuvenate and differentiate.

The auxin may be a naturally occurring auxin but is preferably a synthetic auxin. Typical synthetic auxins include but are not limited to 2,4-dichlorophenoxyacetic acid (2,4-D), 2,4,5-trichlorophenoxyacetic acid (2,4,5-T), 4-(2,4-dichlorophenoxy) butyric acid (4-(2,4-DB)), 2-(2,4-dichlorophenoxy)propionic acid (2-(2,4-DP)), sodium 2,3,6-trichlorophenylacetate, sodium 2-(2,4-dichlorophenoxy)ethyl sulphate, sodium 3-(2,4,5-trichlorophenoxy)propionate, 3-indole butyric acid, 1-naphthaleneacetamide and 1-naphthalene acetic acid (NAA). As an example of a naturally occurring auxin there may be mentioned 3-indoleacetic acid (IAA).

When treating seedlings with an auxin I prefer to use also a cytokinin. Examples of suitable cytokinins are kinetin, zeatin and benzyladenine. Typically an amount of cytokinin is used in the range of from about 0.0001 micrograms up to about 0.01 mg per liter. Usually it is satisfactory to use amounts of cytokinin in the range of from about 0.001 mg to about 0.004 mg per liter.

It is also possible to include, in addition to the chosen auxin and the chosen cytokinin, a gibberellin such as gibberellic acid. However, if a gibberellin is included, then lesser amounts of auxin and cytokinin should be used than in the absence of the gibberillin.

If a cytokinin, and possibly also a gibberellin is included in the growth medium together with the first auxin, then I have found it desirable to include it or them also in the growth medium containing the second auxin. In this way the only change made to the medium during mitotic cell formation, in this case tumor, is the change of auxin. By this inventive process, critical surface changes are induced at the cell membrane since the endogenous hormones are stimulated. When the "vegetative point" of the shoot, the "growing point" of the root, of a plant, as example, of the family Solanaceae, Erythroxylaceae, Papaveraceae, Apocynaceae, at any stage of its ontogenesis is submitted successively to hormonal action (auxin activity) by means of two different hormones, a tumor arises which grows rapidly. The formation of this tumor is less dependent on the concentration and the nature of these hormones, but rather is a result of the duality of the treatment.

When the chosen plant material comprises seeds, these are preferably first disinfected by any of the known techniques, e.g. by contact with bromine water or with a dilute solution of sodium or calcium hypochlorite. The seeds must then be allowed to germinate on a filter paper impregnated by distilled water only under sterile conditions, preferably under controlled environmental conditions. Preferably doubled distilled water is used. In one technique, the resulting seedlings are then preferably transplanted onto a suitable solid medium. The controlled environmental conditions are preferably maintained after transplantation. The medium used should contain those mineral salts required for development of the plant in appropriate quantities and also the first auxin, e.g. NAA. The medium preferably also contains traces of vitamins. Any conventional solid plant growth medium can be used to which the first auxin is added.

The period of time during which the seedlings are exposed to the first auxin may vary from about 1 to about 12 days but preferably is in the region of from about 5 to about 10 days. Eight days is generally suitable under appropriately controlled environmental conditions, as during this period of growth vigorous development of roots is generally observed.

After this period of growth in the presence of the first auxin the seedlings are exposed to the second auxin, e.g. 2,4-D. This can be effected by transplanting the seedling onto a similar solid medium which is essentially identical to that previously used except for the different auxin.

Liquid culture techniques can be used in place of solid culture techniques for the seedling. Thus, the seeds are germinated in a test tube on a filter paper "bridge" dipping into distilled water only. After the seedling has grown to a suitable size, the distilled water (double distilled water preferably) is replaced by a suitable liquid medium containing the first auxin. The change of auxin is particularly simply achieved when a liquid culture technique is employed since in this case, it is merely necessary to drain off the liquid medium containing the first auxin and introduce a similar liquid medium containing the second auxin.

The first and second auxins can be used in amounts of, for example, about 0.0001 mg up to about 1 mg per liter, more usually in the region of about 0.0005 mg to 0.2 mg per liter. Frequently, it is sufficient to use amounts of auxin within the range of from about 0.0005 mg to about 0.1 mg per liter. Less than about 0.0005 mg per liter of auxin does not usually produce any significant effect. Since auxins differ in potency the optimum amount to be used will vary with the type of plant and from auxin to auxin. Care must be taken not to use too much auxin because many synthetic auxins have a herbicidal action at higher concentrations.

Tumor formation, for the reason explained, generally becomes evident amongst at least a proportion of the seedlings after a further period of growth under the influence of the second auxin. This period may vary according to the environmental conditions under which the seedlings are grown but under favourable conditions may be within the range of from about 5 days to about 10 days. After the first observance of tumor formation growth in the presence of the second auxin may be continued for a further period of, for example, about 5 days to about 10 days until a convenient stage for the next process step is achieved.

The next process step, rejuvenation, is a very important aspect of my discovery. The fact of cutting an explant from a mother plant, whatever it is, induces a rejuvenation process, but this step back through juvenility does not produce embryonic cells. To date, it has always been thought that meristematic cells are embryonic cells and that one could grow a plant from a meristematic cell in culture directly. Although plantlets have been obtained in this manner, this was without embryogenesis and as a result of regeneration. Meristematic cells, as callus cells and tumor cells, are mitotic cells with different level of dedifferentiation. I have discovered that mitotic cells must be first rejuvenated environmentally in order to achieve embryogenesis.

Leaf and roots are nutritionally interdependant, the exchange between them of essential metabolites facilitating feedback control of growth and development. This complementation leads me to the conclusion that only differentiated cells leading to the formation of a new plant by embryogenesis can produce the same secondary metabolites synthesized by the whole plant. For example, carbohydrates, primary metabolites are synthesized in the leaf whereas N-absorption is effected by the roots, its metabolism is mainly achieved in the roots. Buds or roots that develop on cultured tissues, both callus and cell suspension, undergo characteristic structural changes in the development of the cytoplasmic organelles—incomplete morphogenetic development of chloroplasts as revealed by electron microscopic studies for example—and subsequently in the function of these organelles. Buds and roots that develop on callus or cell culture are often not connected by vascular tissue (because the roots are formed under the influence of the bud from adjoining cells). But if the roots are formed out of the young bud (the case when a meristem of vegetative mother plant is inoculated), roots are formed and a plantlet arises which can grow into a mature plant. This technique used for plant propagation in the agricultural and horticultural field is of course not suitable for biochemical purposes.

I have discovered that if mitotic cells are rejuvenated, made juvenile, and taken back to the embryonic state by means of controlled environmental factors, that I can then produce from the rejuvenated cells normal healthy embryos and thence plants, each cell either of somatic or generative origin being capable of producing an entire plant. Thus, I take the mitotic cells, whether induced from an explant or from seedlings and transfer them to a liquid culture medium and preferably, with shaking or some other suitable form of agitation prevent settling or "clumping" and facilitate gas uptake and release. By carefully controlling the environmental conditions, the cells are rejuvenated to the embryonic stage and differentiation is induced. In this way, a cell culture of single embryonic plant cells from the chosen plant are produced. Rejuvenation and differentiation conveniently proceed for a period of time of from about 10 days to about 14 days following which the cells may be harvested for extraction of their metabolite content such as alkaloid content. Alternatively, the mitotic culture may be propagated by repeated subculturing and only a portion thereof may be used at intervals for the steps of rejuvenation and differentiation.

Differentiation of the cells may or may not occur spontaneously. Thus, a few of the cells may become partially differentiated leading to development of a greenish or reddish tint to the cell (due to the formation of chorophyll and some aromatic compounds). However, I have discovered that cell differentiation can be positively induced by appropriate control of the environmental conditions, and particularly of the lighting and temperature conditions.

It is known that the mitotic cells contain only traces of metabolites such as tropane alkaloids and I have verified this fact. However, cells can synthesize metabolites such as tropane alkaloids after differentiation has occurred. Thus, differentiated cells will usually be found to have alkaloid contents of between about 0.8% and about 1% by weight based upon the harvested dried cell culture material, i.e. of the same order of magnitude as the alkaloid content of whole plant material. Further, I have found that, if the differentiated cells develop to form embryoids, the tropane alkaloid content of the harvested material normally increases to a somewhat higher percentage than this. If the development of the new plantlets is allowed to continue beyond the embryo and seedling stages, the alkaloid content of the harvested material falls to a lower percentage again. Starting from *Hyoscyamus muticus* L. or *Hyoscyamus aureus* L. I have obtained from embryoid-containing cell cultures yields of alkaloid corresponding to between about 1% and about 5% by weight based on dried harvested plant cell material. In the case of embryoid-containing cultures obtained starting from *Duboisia leichardtii* or

*Duboisia myoporoides* the alkaloid yield may be as high as about 8% to about 10% by weight based on dried harvested cell material.

Harvesting is thus best effected soon after differentiation has occurred, and especially when the embryos are completely formed.

Tropane alkaloids are usually most easily obtained when the majority of the cells are at the embryoid stage, that is to say when torpedo shaped embryoids are visible, but before the full development of seedling (i.e. after the formation of two cotyledons). If the majority of the differentiated cells are allowed to develop beyond the embryo and seedling stages and to produce plantlets, the recovery of alkaloids generally becomes somewhat more complicated. Usually the pattern of alkaloids formed changes somewhat as the plantlets develop. Major alkaloids predominate at early stages of development with minor alkaloids appearing at their highest levels at the embryo and seedling stages and gradually diminishing as the plantlet grows further. Additionally, secondary metabolites appear in the embryos and are easily extracted at good yields. At later stages, the extraction process comprises more steps (e.g. fat, pigment elimination) and thus the more steps there are, the less the yield will be of the desired metabolite. Extraction of alkaloids is thus simplest at the embryoid or seedling stage. However, the optimum moment for harvesting is to some extent dependent on the particular metabolite of interest. It may be better to delay harvesting beyond the embryoid stage if the metabolite of interest reaches higher proportions at a later stage, but this optimizing can be easily determined by conventional research.

I have found in my work on the plants of the species Hyoscyamus spp. and Duboisia spp. that the growth of the plants is greatly influenced by light and to a lesser extent by temperature and humidity. In a similar way light has an influence on mitotic tissue formation and growth and on the growth and development of cells in liquid cell culture. Temperature is also of significance in this respect. In particular differentiation of the cells can be significantly influenced by appropriate control, inter alia, of the lighting conditions.

In considering the lighting conditions used in my process, three parameters are of particular importance, viz. the spectrum, the energy level and the day length.

The overall spectrum of the light to which the plants, seeds, seedlings, mitotic tissue, cells and embryos are exposed can be controlled by selecting the types of lamps used for irradiation, using for this purpose the spectral data published by the manufacturers. Suitable lamps can be selected from fluorescent tubes of various types, and incandescent lamps, particularly tungsten filament, xenon, and iodine vapour lamps.

Filters can be used to adjust the spectrum if desired. I prefer to use light that approximates as closely as possible to the light conditions that prevail in the plants normal habitat. Thus, for the plant *Hyoscyamus miticus* L. I prefer to use light that approximates to tropical sunlight such as is found in the Sahara and similar sub-desert regions.

Light which approximates to tropical sunlight can be obtained using a mixture of fluorescent and incandescent tungsten filament lamps.

Light that is richer in far red than red can be produced by using incandescent tungsten filament lamps alone, by using xenon lamps, or iodine vapour lamps, or by using "Grolux" tubes.

In a first preferred regime, irradiation is carried out so as to simulate long days of topical sunlight, e.g. irradiation with simulated tropical sunlight for periods of about 16 hours, interspersed with periods of night lasting, for example, about 8 hours. These plants are day neutral plants with preference for long day period.

In an alternative second regime, long days can be simulated by irradiation with simulated tropical sunlight for periods of, for example, 9 days of light followed by 15 hours of which 7 hours is incandescent light, which is richer in far red and is provided by tungsten filament lamps, and the remaining 8 hours in darkness.

In a third regime, a 9 hour period of light is followed by 15 hours of incandescent light (and no periods of darkness).

In a fourth regime, a 16 hour day provided by a ceiling consisting of a mixture of fluorescent "Grolux" tubes and incandescent tungsten filament lamps is followed by an 8 hour night.

The photoperiod is selected in accordance with the requirements of the whole plant in its natural habitat, as for example, tissue or cells of *Hyoscyamus muticus* L. a photoperiod of preferably 16 hours or more but less than 24 hours per day of 24 hours. If growing is carried out under a photoperiod of 24 hours, a physiological "tiring" results. For *Hyoscyamus aureus* L. in culture a photoperiod of 16 hours is optimum (this is a strict long day plant in its habitat); *Papaver bracteatum* L. requires a photoperiod of 9 hours; and *Trypterigium wilfordii* also requires a photoperiod of 9 hours.

The energy level can be varied within wide limits e.g. from 2,000 up to 400,000 ergs per sq. cm. per second or more. However, I have found that energy levels within the range of 100,000 to 200,000 ergs per sq. cm. per second, e.g. about 140,000 egs per sq. cm. per second, are preferable for plants (and plant material derived therefrom) such as members of the species Duboisia spp. and Hyoscyamus spp.

During each of the stages of my process the temperature is an important consideration and its plant has its own temperature requirements generally a lukewarm and constant temperature (27° C.) is maintained for the germination and tumor induction stages. The mitotic cells, once obtained, are subjected to an alternated temperature, preferably. In this way, rejuvenation is induced. Using plant material from *Hyoscyamus muticus* spp. a temperature of 27° C. is maintained during germination and tumor induction and the mitotic cells are subjected to an alternated regime of 27° C./17° C. (day/night).

The humidity should desirably be maintained during growth of plants, explants, cells, tumor, etc. at a level of about 70% relative humidity. However the humidity can vary from about 40% up to about 70% relative humidity.

Harvesting and extracting can be done by any known method e.g. freeze-drying for harvesting, gravimetric techniques, partition chromatography (Kieselguhr), their layer chromatography for extraction.

The plant material from which the messenger, a cinnamic derivative, is obtainable are from Solanacaeae and Erythroxylaceae families e.g. the species Hyoscyamus spp. of Duboisia spp. being the richest. The species Hyoscyamus spp. includes *Hyoscyamus niger* which is found in Europe and the tropical plants *Hyoscyamus muticus* L. and *Hyoscyamus aureus* L. The species Duboisia spp. includes the plants *Duboisia leichardtii* and *Duboisia myoporoides*.

When whole plant material is chosen as the starting material in the process of the invention and has been grown according to the invention extraction can be carried out using any known extraction technique for cinnamic derivative or glucoprotein e.g. column chromatography (Sephadex 200 and G25). Preferably the process of the invention is carried out using the embryogenesis in vitro process previously described. That is plant material of the species Dubosia spp. or Hyoscyamus spp. is caused to produce a tumor and thereof is rejuvenated. The cell culture is treated with a selected spectrum of light in order to induce qualitative and quantitative changes in the metabolic pattern. I have found that if the active form of the phytochrome is excited, in the case of these plants, growth is regulated, while in the case of mitotic cells differentiation is induced. Thus, I have discovered that by irradiating the cell culture with light richer in far red than red (maximum of action at 730 nm) the active form of the phytochrome is excited and the corresponding physiological effects are observed in the cell culture and the cinnamic derivative is generated at a high yield. This is also true for the whole plant.

Light that is richer in far red than red can be produced by using incandescent tungsten filament lamps alone, by using xenon lamps, or iodine vapour lamps, or by using "Gro lux" tubes. Monochromators or filters can be used to enhance the spectrum in the far red and infra red regions.

Depending on the light spectrum that is desired, the type of lighting used in the invention can be provided by a ceiling selected from:
(1) a mixture of fluorescent "Atlas daylight" and incandescent tungsten filament lamps,
(2) a mixture of fluorescent "Fluora" or "Gro lux" lamps and incandescent tungsten filament lamps,
(3) Xenon lamps,
(4) Iodine vapour lamps,
(5) an equal combination of xenon lamps and iodine vapour lamps.

I prefer to use lighting regimes that give to the plant photo periods.

In a first preferred regime, irradiation is carried out with artificial tropical daylight (ceiling (1)) for about 9 hours, immediately followed by 7 hours of monochromatic far red light or light from incandescent tungsten filament lamps, followed by 8 hours of darkness to complete the day of 24 hours.

In a second regime a 9 hour period of artificial tropical daylight (ceiling (1)) is followed by 15 hours of the monochromatic far red light or light from tungsten filament lamps to complete the day of 24 hours.

In a third regime a 16 hour photo period is provided by one of ceilings (2) to ( 5) above is followed by 8 hours of darkness.

In a fourth regime one of ceilings (2) to (5) above is used for continuous lighting (24 hours per day of 24 hours).

In plants rich in this "messenger", by simply inducing a daily rythm or by setting a physiological clock in the cells, as example, with preselected day/night temperature, photo period, the differentiation process is automatically conducted.

It is convenient to effect all stages of plant growth and/or cell culture in a controlled environment such as can be provided in a so-called "phytotron". The energy level and humidity are controlled in the manner already described.

As already mentioned the cinnamic derivative of the invention appears to be capable of inducing differentiation of cells in a wide variety of plants. Thus, in another of its aspects, the invention provides a process for inducing differentiation in plant cells in a culture thereof which comprises culturing the plant cells in the presence of differentiated cells containing the cinnamic derivative, such as those derived from the species Hyoscyamus spp. or Duboisia spp. Wholly or partially differentiated cells derived from the species Hyoscyamus spp. or Duboisia spp. may be added to the culture of the cells in which it is desired to induce differentiation.

In yet another aspect of the invention, there is provided a process for inducing differentiation in plant cells in a culture thereof which comprises adding to the culture a physiologically effective amount of the cinnamic derivative of the invention and maintaining the culture under suitable conditions of cell growth.

The process of embryogenesis in vitro can be used for plants other than members of the species Hyoscyamus spp. or Duboisia spp., virtually any plant source. Typical of such plant sources are members of the species Papaver spp., Catharantus spp., Rauwolfia spp., Cassia spp., Ricinus spp., Agave spp. and Piptadenia spp. These species are of particular importance since members of them yield important medicinal compounds, among which may be mentioned alkaloids, antitumoral agents, immuno-suppressive agents, saponins, steroids and hert glycosides and so on.

The invention will be further illustrated by the following Examples.

The standard synthetic medium used in the Examples (modified Wood and Braun's Medium) is made up from the following stock solutions:

(a) White's solution (amounts in 2 liters of solution)
$Ca(NO_3)_2.4H_2O$ —5.96g
$Na_2SO_4.10H_2O$—9.16g
KCl—1.30g
$NaH_2PO_4.2H_2O$—0.628g
$MgSO_4.7H_2O$—14.96g
$MnSO_4.4H_2O$—0.132g
$ZnSO_4.4H_2O$—0.054g
$H_3BO_3$—0.030g
KI—0.014g
$H_2O$—To 2 liters.

(b) White's II solution (amounts in 2 liters of solution)
Glycine—0.30g
Nicotinic acid—0.05g
Thiamine hydrochloride—0.01g
Pyridoxine hydrochloride—0.01g
$H_2O$—To 2 liters (c) Wood and Braun's solution (amounts in 2 liters of solution)
KCl—16.90g
$NaNO_3$—36.00g
$MgSO_4.7H_2O$—20.00g
$NaH_2PO_4.2H_2O$—6.93g
$H_2O$—To 2 liters To make up 1 liter of the standard synthetic medium the following constituents are mixed:
White's I solution—100 ml
White's II solution—10 ml
Wood and Braun's solution—100 ml
$(NH_4)_2SO_4$ (0.79 g/liter)—10 ml
Glucose—30g (or Sucrose 20g)
Agar—10g
1 M inositol solution—10 ml
Fe EDTA complex solution—1 ml H₂O—To 1 liter
(EDTA is ethylene diamine tetraacetic acid; the Fe EDTA complex solution contains 7.84 mg of the complex per liter).

Example 1

*Hyoscyamus muticus* L. plants are grown from seed by hydroponic culture using a mineral salt solution (see P. Chouard and M. Tran Thanh Van, C.R. Acad. Sc. Paris, 259 (1964), p. 4783–4786), at a pH of 5.1 to 5.4 under specified light, temperature and humidity conditions. The spectrum of the artificial light used is as complete as possible so as to simulate tropical daylight. The infra red/red ratio is approximately 1. The day length is controlled to e 16 hours followed by a night period of 8 hours. The light is furnished by an artificial lighting ceiling of phytotronic type made up of a mixture of fluorescent tubes, i.e. "Atlas" daylight tubes, and of incandescent tungsten filament lamps. The energy level of the artifical daylight is controlled at about 140,000 ergs per square centimeter per second. The temperature is held at 27° C. The relative humidity is 70%.

When the plants have grown to a suitable stage, floral stem or meristematic tissues are used as explant and placed under sterile conditions in a 250 ml Erlenmeyer flask containing about 50 ml of a solid medium consisting of the standard synthetic medium (modified Wood and Braun's Medium) to which is added 7 to 10% by weight of agar. No phytohormone is added to this medium. The pH of the medium is 5.1 to 5.4 If the explant is from another origin, phytohormone is added to the medium at a final concentration of 0.001 mg/l of Kinetin and 0.02 mg/l of 2,4-D. The same lighting and temperature conditions and the same photo period are maintained. In due course callus formation can be observed.

This mitotic tissue is transferred into a fresh similar nutrient and allowed to grow under the same controlled lighting conditions and a regime of day and night temperature of 27° C./17° C.

Some small portions of this embryonic tissue are transferred to a number of 250 ml Erlenmeyer flasks each containing about 50 ml of the liquid modified Wood and Braun's Medium. The flasks are gently shaken continuously to encourage gas exchange or release and to prevent "clumping" or settling of the cells. The cultures are then subjected to the same temperature and light conditions last mentioned.

The cells multiply and take on a greenish, reddish or pinkish hue showing that some differentiation has occurred. By modifying the spectral quality of the light: 9 hours of trophic light immediately followed by 7 hours of incandescent supply, during 1 to 8 days a complete redifferentiation with embryos formation at different stages of development are obtained about 100,000 per flask. The differentiation process can be stopped or pursued as desired. In the first case the harvesting or extraction process can take place. Total duration is less than four months.

EXAMPLE 2

Seeds of *Hyoscyamus muticus* L. are sterilized by brief immersion in 10% bromine water. They are then transferred to damp (double distilled water) filter paper contained in a Petri dish, which is then placed in a growth chamber maintained at 27° C., and irradiated under a regime which consists of 9 hours of simulated tropical daylight, immediately followed by 7 hours illumination with tungsten filament incandescent lamps and then by an 8 hour period of darkness. The light used to provide the simulated daylight is provided by an artificial lighted ceiling of phytotronic type made up of "Atlas" daylight fluorescent tubes and incandescent, tungsten filament lamps. The energy level is about 140,000 ergs per square centimeter per second. Within 24 hours of commencing this treatment most of the seeds germinate. The petri dish is then subjected to a normal lighting regime of 16 hours of trophic light followed by 8 hours of darkness. After 7 days the seedlings are enough developed for transplantation.

The seedlings are transplanted, still under sterile conditions, onto a snythetic solid medium made up from the standard mineral salt medium used in Example 1 and containing 10% by weight of agar, to which is added 0.01 mg per liter of NAA and 0.001 mg per liter of kinetin. Illumination of the seedlings is continued as before and the temperature is maintained constant at 27° C.

After 10 days of this regime ten seedlings have developed a vigorous root growth and then transplanted to a similar solid medium but containing 0.02 mg per liter of 2,4-D instead of the 0.01 mg per liter of NAA. After 3 days of further growth, still under the same environmental conditions, tumorous tissue formation is visible. This tissue growth is continued for 7 days. At this stage the roots of the plantlet are covered by an off-white fluffy tumor. If some of the tumor cells are transferred onto another portion of the same 2,4-D-containing solid medium they continue to grow very fast.

Some of the tumor cells are thereafter transferred to a modified Wood and Braun's Medium, with or without auxin, and cultured by the method of Example 1. Harvesting by the method of Example 1 yields similar results.

EXAMPLE 3

Examples 1 and 2 were repeated with *Hyoscyamus aureua* using a photo period of 16 hours, a day of 24 hours and a day/night temperature of 22° C./17° C. and yielded better results.

EXAMPLE 4

Seeds of *Duboisia myoporoides* which have been sterilized by dipping briefly in 10% bromine water are placed individually on filter paper "bridges" arranged to dip into double distilled water in corresponding test tubes under sterile conditions. The seeds are irradiated at 27° C. at an energy level of 140,000 ergs per centimeter per second with artificial tropical daylight of the type described in Example 1 for 9 hour photo periods, interspersed with 15 hour periods of darkness. Seedlings develop and after 7 days the distilled water in each tube is poured out and replaced by a quantity of synthetic liquid medium (modified Wood and Braun's Medium) containing 0.01 mg per liter of NAA and 0.001 mg per liter of kinetin. The same temperature and lighting conditions are maintained for a further 7 days, following which the medium is replaced by a similar liquid medium containing 0.02 mg per liter of 2,4-D in place of the NAA but otherwise identical with the NAA-containing medium. Tumor cells form and growth is maintained under the same conditions for a further 14 days.

The tumor cells are then cultured in liquid medium under the lighting conditions used in Example 1 and a day/night temperature of 22° C./12° C. The cells are thereby rejuvenated and differentiated and thereafter harvested by the methods described in Example 1. Similar results are obtained.

EXAMPLE 5

A wheat cell culture is prepared in an auxin-free liquid medium by conventional methods. Approximately 10 ml of the solution obtained from the column in Example 1 containing the cinnamic derivative is added to the wheat cell culture. The resulting culture is maintained at 25° C. constant with shaking and is illuminated according to the following regime: 24 hours of a ceiling of phytotronic type. After 4 to 6 weeks large numbers of torpedo shaped embryos are visible.

EXAMPLE 6

A wheat cell culture is prepared in an auxin-free liquid medium by conventional methods. To this are added differentiated cells from *Hyoscyamus aureua* L. The culture is then grown under the conditions used in Example 5 except the regime was 9 hours "Atlas" daylight fluorescent lamps and tungsten incandescent lamps followed by 7 hours tungsten filament incandescent lamps alone followed by 8 hours darkness. Similar results are obtained.

EXAMPLE 7

A cell culture in an auxin-free liquid medium is produced by conventional methods from *Catharanthus roseus* L. Differentiated cells from *Hyoscyamus muticus* L. are added to the culture which is then grown under the conditions of Example 6. After some weeks differentiated cells can be observed under a microscope.

Furthermore, in a u.v. microscope the presence of fluorescent alkaloids (hence alkaloids other than tropane alkaloids) can be detected. These alkaloids are further identified by TLC giving a positive reaction in the Dragendorf reaction, thus providing confirmation of redifferentiation of the *Catharanthus roseus* L. cells.

EXAMPLE 8

A sycamore cell culture (5 years old) prepared in a conventional manner in a liquid auxin-free medium is taken. Cells from *Hyoscyamus muticus* L. are added and the culture is grown under the conditions of Example 6. After some weeks phenolic compounds can be detected in the media, indicating that some of the sycamore cells at least have been induced to redifferentiate.

EXAMPLE 9

10 ml of the chromatographically partially purified cinnamic derivative of Example 1 is added to the culture medium of an epidermic tissue culture of *Thorenia furnieri* and in another case 100 ml of thepartially purified cinnamic derivative of Example 1. In the first case, a high percentage of the nucleus of the cells after 24 hours undergo mitosis. In the second case no activity was observed.

EXAMPLE 10

The solution of cinnamic derivative isolated in Example 1 is subjected to bactericidal tests. Antibacterial activity is shown against *E. coli, B. Linchiformis* and Azotobacter, B. aureus.

EXAMPLE 11

The procedure of Example 2 is repeated using *Duboisia leichardtii.* Similar results are obtained.

Figure 1:
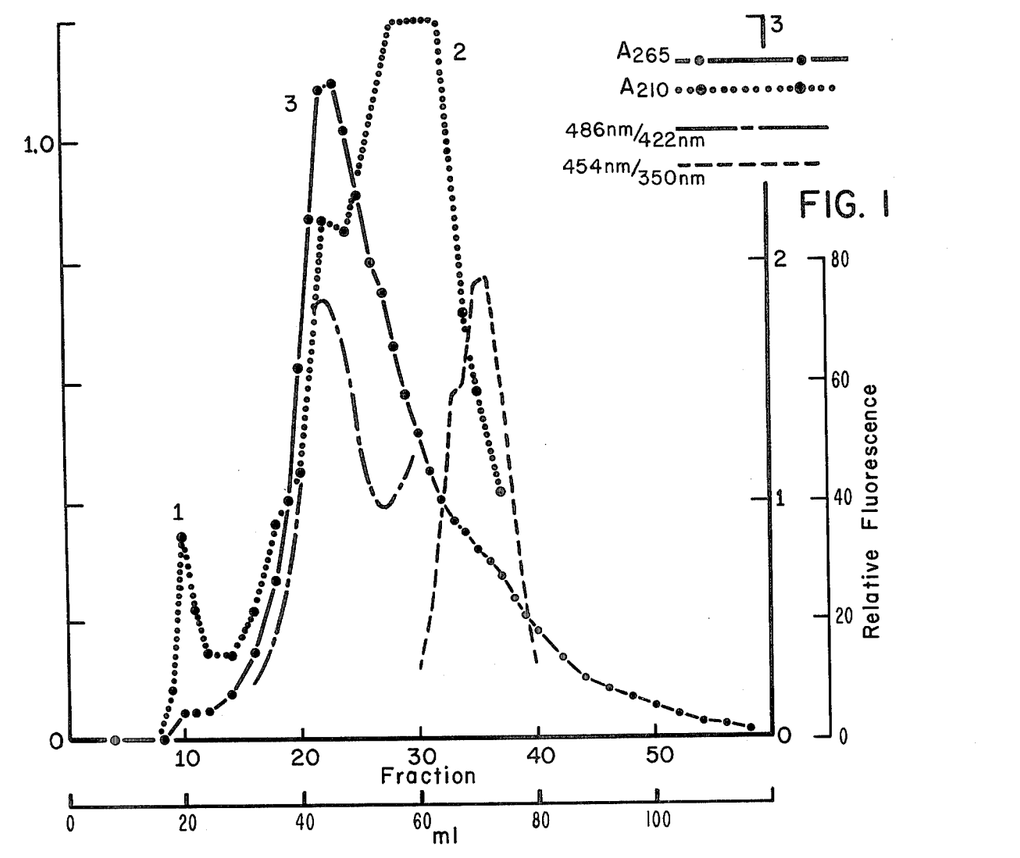
Figure 2:
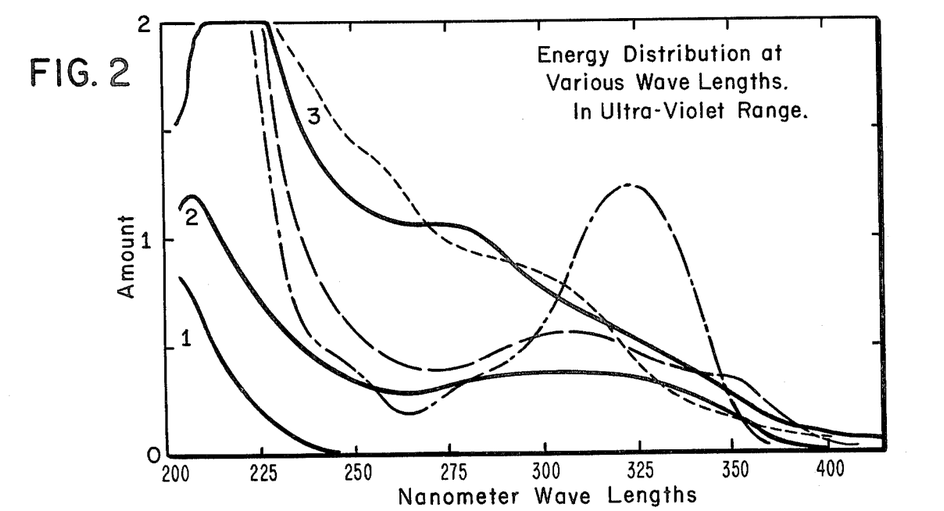

FIGS. 1 and 2 show the spectrum in ultraviolet or the relative fluorescence of the novel compounds and 5HFA (Hydroxy ferulic acid). Curve 1 is a novel steroidal compound which exhibits on cellulose thin layer chromatography an Rf value in acetone of 0.01 and a light blue fluorescense in ultraviolet light. On silica gel thin layer chromatograpyy with the solvent system ethylacetate/petroleum either (7:3), it exhibits an Rf value of 0.01. Curve 4 is 5-Hydroxyferulic acid (5HFA). Curve 3 is the novel non-cytotoxic metabolite cinnamic derivative, whose bio-synthesis is closely dependent on PAL (Phenylalanine amonia lyase) from plant material of the species Hyoscyamus and Duboisia, the novel metabolite being a growth regulator, and being effective for inducing cell differentiation in plant cells, and possible having anti-tumoral properties, the novel metabolite appearing to be a cinnamic derivative chemically related to 5-Hydroxyferulic acid (5HFA) which chromophor exhibits on silica gel thin layer chromatography an Rf value in ethylacetate/petroleum ether (7:3) of approximately 0.7 and a yellow fluorescence in ultraviolet light. Curve 2 is another novel metabolite (cinnamic derivative) also dependent on PAL which is the same system has an Rf value of 0.4 and a strong blue fluorescense in u.v. light. For curve 3 and curve 2, on cellulose and acetone as solvent, the compound of curve 2 exhibited an Rf value of 0.7 and the compound of curve 3 exhibited an Rf value of 0.4.

The invention will be further illustrated by reference to the following Examples.

The standard synthetic medium used in the Examples (modified Wood and Braun's Medium) is made up from the same stock solutions previously described.

EXAMPLE 12

*Hyoscyamus muticus* L. plants are grown in a controlled temperature room from seed by hydroponic culture using a mineral salt solution (see P. Chouard and M. Tran Thanh Van, C. R. Acad, Sc. Paris, 259 (1964), p,. 4783-4786), at a pH of 5.1 to 5.4 under specified light, temperature and humidity conditions. The spectrum of the artificial light used is as complete as possible so as to simultate tropical daylight. The day length is controlled to be 16 hours per day of 24 hours. The ceiling is furnished by an artificial lighting of phytotronic type made up of a mixture of fluorescent tubes, i.e. "Atlas" daylight tubes, and of incandescent tungsten filament lamps. The energy level of the artificial daylight is controlled at about 140,000 ergs per square centimeter per second. The temperature is held at 27° C. The relative humidity is 70%.

When the plants have grown to a suitable stage, explants are taken and placed under sterile conditions in a 250 ml Erlenmeyer flask containing about 50 ml of a solid medium consisting of the standard synthetic medium (modified Wood and Braun's Medium) to which is added 7 to 10% by weight of agar. When floralstem or meristematic tissue are used, as explained, no addition of hormone in the medium is necessary. If the explant is from another origin, phytohormone is added to the medium at a final concentration of 0.001 mg/l of kinetin and 0.02 mg/l of 2,4-D. The same lighting and temperature conditions are the same day length are maintained. In due course callus formation can be observed.

Some of the callus cells are transferred under sterile conditions to another 250 ml Erlenmeyer flask containing a further similar quantity of the solid medium. The mitotic tissue continue to grow under the same controlled lighting and temperature conditions.

Portions of the resulting callus are transferred to 250 ml Erlenmeyer flasks each containing about 50 ml of the liquid culture medium (modified Wood and Braun's Medium). The flasks are capped and gently shaken continuously to encourage gas exchange or release and to prevent "clumping" or settlibng of the cells. These flasks are then subjected to different procedures.

(a) Some flasks are maintained in the dark at 27° C. and cell culture is effected in the dark for 10 days. Cell culture is not limited during this period by the supply of oxygen. After 10 days' growth, extraction is carried out as described by W. C. Evans and M. W. Partridge in the *Journal of Phyarmacy and Pharmacology*, Vol. 4, Page 769 (1952). A very small amount of a mixture of tropane alkaloids is obtained which can be identified by conventional methods, e.g. by thin layer chromatogrphy on activated alumina. The yield of alkaloids chromatography on activated alumina. The yield of alkaloids corresponds to less than 0.1% by weight based on dried harvested cell material and consists mainly of atropine and hyoscyamine.

(b) A second group of flasks is also kept 10 day at 27° C. in the dark and the resulting callus cell culture is multiplied four times by sub-culturing at intervals of 10 days. A similar yield to tropane alkaloids is obtained from the final subculture upon harvesting by the method described in Example 12(a) above.

(c) A further group of flasks is subjected at 27° C. to the same lighting regime (i.e. simulated tropical sunlight and 16-hours day (length) as is used during plant growth. The energy level is again 140,000 ergs per sq. sm. per second. Cell growth is somewhat faster than when following the procedure of Example 12(a) and a few of the cells spontaneously undergo differentiation, which can be detected by the reddish or greenish tinge of such cells. Upon harvesting by the method described in Example 12(a) after 10 days' growth, the yield of tropane alkaloids is again about 0.1% by weight based on dried harvested material.

(d) Yet another group of flasks is subjected to a day/night temperature of 27° C./17° C. and to the following lighting regime: 9 hours simulated tropical sunlight, 7 hours irradiation from tungsten filament lamps alone, 8 hours darkness. This regime is maintained for 7 days. After 24 hours a significant number of the cells have become rejuvenated and differentiated and after 7 days the majority of the cells have developed into embryoids. The spectral quality of the light is modified to a normal ceiling for one week. Upon harvesting by the method of Example 12(a), the yield of alkaloids (mainly atropine and hyoscyamine) is approximately 250 mg (or approximately 3% by weight based on dried harvested material).

EXAMPLE 13

Examples 12(a) to 12(d) are repeated using seeds of the plant *Hyoscyamus aureus* L. Similar yields of tropane alkaloids are obtained in each case but consisting predominantly of scopolamine.

EXAMPLE 14

Examples 12(a) to 12(d) are repeated, using seeds of the plant *Duboisia leichardtii* or *Duboisia myoporoides*, except that day and night temperatures of 22° C. and 12° C. are used. The (a) to (c) procedures give minimal alkaloid yields; the (d) procedure gives about 9%.

EXAMPLE 15

Seeds of *Hyoscyamus muticus* L. are sterilized by brief immersion in 10% bromine water. They are then transferred to damp filter paper contained in a Petri dish, which is then placed in a sterile cabinet maintained at 27° C., and irradiated for a period of 9 hours of trophic light using the first ceiling of Example 12, a period of 7 hours of incandescent light and an 8 hour period of darkness. The energy level is about 140,000 ergs per square centimeter per second. After one day, most of the seeds germinate. The spectral quality of the light is modified and a photo period of 16 hours of trophic light is used with 8 hours darkness. After 7 days the seedlings are large enough for transplantation.

The seedlings are transplanted, still under sterile conditions, onto a synthetic solid medium made up from the standard mineral salt medium used in Example 12 and containing 10% by weight of agar, to which is added 0.01 mg per liter of NAA and 0.001 mg per liter of kinetin. Illumination of the seedlings is continued as before and the temperature is maintained at 27° C. constant.

After 7 days of this regime the seedlings have developed a vigorous root growth and are transferred to a similar solid medium but containing 0.02 mg per liter of 2,4-D and the same amount of kinetin. After 5 days of further growth still under the same environmental conditions, tumor formation is visible. Tumorous tissue growth is continued for 7 days. At this stage the roots of the plantlet are covered by an off-white fluffy tumor. If some of the tumor tissue is transferred onto another portion of the same 2,4-D-containing solid medium they continue to grow very fast.

Some of the tumor tissue is thereafter transferred to an auxin-free synthetic liquid medium (the modified Wood and Braun's Medium) and cultured by the methods described in Examples 12(a) to 12(d), similar results are obtained.

EXAMPLE 16

The procedure of Example 15 is repeated using seeds of *Hyoscyamus aureus* L. Similar results are obtained.

EXAMPLE 17

The procedure of Example 15 is repeated using seeds of *Duboisia leichardtii* and of *Duboisia myoporoides*. In each case the yield is as follows based on dried harvested cell or embryoid material:
Procedure of Example 12(a) 0.1% approximately
Procedure of Example 12(b) 0.1% approximately
Procedure of Example 12(c) 0.1% approximately
Procedure of Example 12(d) 9% approximately

EXAMPLE 18

Seeds of *Duboisia myoporoides* which is a short day plant are grown like in Example 12 except using a 9 hour photo period of trophic light. Rejuvenation and differentiation is carried out by day/night temperature of 22° C./12° C.

The resulting cell culture harvested by the methods described in Examples 12(a) to 12(d) gives yields similar to those obtained in Example 17.

EXAMPLE 19

Using either the techniques of Example 12 (explants) or Example 5 (seeds), the following three higher plants *Tripterygium wilfordii, Putterlichia verrucosa* and *Mayte-*

*nus buchananii* each give embryonic cells and the metabolites synthesized by the respective whole plant. The conditions are the same except that the temperature used is 22/14° C. and a short day (9 hrs.).

EXAMPLE 20

A portion of the embryonic cells of each of the three plants of Example 9, young cells rejuvenated of these plants, and explants are cultivated in mixed fermentation with fungi imperfecti and each leads to the formation of metabolites which were tested to have anti-neoplastic properties.

As a further aspect of my invention, changes in the pattern of metabolites can be effected by modifying the pH of the nutrient or the mineral balance of the nutrient but only after the embryos have been formed.

Changes may be made to my inventions which do not depart from the spirit and scope of same. Such are deemed to fall within their purview.

What is claimed is:

1. A process for inducing tumor in vitro comprising treating a growing point of a seedling with a first hormone exhibiting auxin activity and thereafter treating the same growing point of the seedling with a second different hormone exhibiting auxin activity.

2. The process of embryogenesis in vitro comprising inducing tumor formation in a plant to produce mitotic cells, rejuvenating the mitotic cells in vitro to produce embryonic cells by means of a controlled environment wherein the temperature range is from about 12° to 27° C., the light energy level is from about 2,000 to 400,000 ergs per sq. cm. per second, the spectral range is up to about 730 nm, for a selected photoperiod, and in a suitable nutrient medium, differentiating the embryonic cells to obtain therefrom embryos.

3. The process of producing metabolites and inducing metabolite pattern changes in a free cell culture comprising establishing a free cell culture of mitotic cells, rejuvenating and differentiating the cells under a controlled environment as set forth in claim 2 and modifying one or more of the factors of the preselected environment.

4. The process of claim 3 wherein the modification occurs after the differentiated cells have reached the embryo stage.

5. The process of claim 3 wherein the modification is selected from one of light spectrum, pH of the medium, temperature, and $O_2/CO_2$ ratio and $CO_2/N_2$ ratio.

6. The process of producing a preselected metabolite comprising the steps of rejuvenating in vitro mitotic cells of a plant producing the preselected metabolite to produce embryonic cells by means of a controlled environment as set forth in claim 2, differentiating the embryonic cells, obtaining embryos therefrom, and extracting the preselected metabolite from said embryos.

7. The process of claim 6 including the further step of modifying the embryos by changing one or more environmental factors to increase the concentration of the preselected metabolite.

8. The process of producing a tropane alkaloid comprising the steps of rejuvenating in vitro mitotic cells of a tropane alkaloid producing plant to produce embryonic cells by means of a controlled environment as set forth in claim 6, differentiating the embryonic cells, obtaining embryos therefrom, and extracting tropane alkaloid from said embryos.

9. The process of claim 8 wherein the concentration of the tropane alkaloid is increased by modifying at least one environmental factor.

10. The process of producing steroidal compounds and novel cinnamic derivatives whose bio-syntheses are closely dependent on PAL, from plant material of the species Hyoscyamus and Duboisia, chemically related to 5-Hydroxyferulic acid (5HFA), comprising the steps of providing plant material of one of the species selected from Hyoscyamus and Duboisia, inducing mitotic cell formation from the said plant material, preparing a cell culture therefrom, rejuvenating the culture under controlled environmental conditions as in claim 6, and redifferentiating the cells.

11. The process of claim 16, further comprising the extraction of at least one steroidal compound or cinnamic derivative.

12. A novel cinnamic derivative produced by the method of claim 11.

13. A process of differentiating undifferentiated plant cells comprising culturing the plant cells to be differentiated with embryonic cells obtained from plant material of one of the species selected from Hyoscyamus and Duboisia.

14. A process of differentiating undifferentiated plant cells comprising mixing the plant cells to be differentiated with a cinnamic derivative derived from plant material of one of the species selected from Hyoscyamus and Duboisia.

15. A process of differentiating undifferentiated plant cells comprising culturing plant cells to be differentiated with differentiated plant cells from another plant.

16. The process of inducing differentiation in undifferentiated Catharanthus sp. cells comprising culturing said cells with differentiated cells from plant material of the Solanaceae of Erythroxylaceae families.

17. The process of inducing differentiation in undifferentiated Papaver sp. cells comprising cultivating differentiated cells from plant material of the Solanaceae or Erythroxylaceae families with said cells to be differentiated.

18. A process of obtaining physiologically active compounds from plants of the Celastraceae family comprising the steps of rejuvenating and differentiating mitotic cells of said plants under the controlled environmental conditions of claim 6, and obtaining from the differentiated cells at least one physiologically active compound.

19. A process of producing metabolites comprising culturing fungi imperfecti with plant material from the family Celastraceae, said plant material being selected from the group consisting of embryos, mitotic cells, differentiated cells, and explants.

20. A process as in claim 19, further comprising extracting said metabolites.

* * * * *